United States Patent [19]

Dakka et al.

[11] Patent Number: 4,965,406
[45] Date of Patent: Oct. 23, 1990

[54] PROCESS FOR THE MANUFACTURE OF BENZOIC ACID AND SALTS THEREOF

[75] Inventors: Jihad Dakka, Triangle; Zoran Amikam; Yoel Sasson, both of Jerusalem, all of Israel

[73] Assignees: Gadot Petrochemical Industries, Inc., Haifa; Yissum Research Development Company of the Hebrew University of Jerusalem, both of Jerusalem, Israel

[21] Appl. No.: 384,065

[22] Filed: Jul. 20, 1989

Related U.S. Application Data

[63] Continuation of Ser. No. 216,116, Jul. 7, 1988, abandoned.

[30] Foreign Application Priority Data

Jul. 23, 1987 [IL] Israel .......................... 83293

[51] Int. Cl.$^5$ ............................. C07L 51/265
[52] U.S. Cl. ........................... 562/414; 562/416
[58] Field of Search ....................... 562/414, 416

[56] References Cited

U.S. PATENT DOCUMENTS

| | | | |
|---|---|---|---|
| 2,865,708 | 12/1958 | Dinsmore | 562/414 |
| 2,883,816 | 4/1959 | Kroll | 53/244 |
| 3,210,416 | 10/1965 | Fragen | 562/414 |
| 3,227,752 | 1/1966 | Olivier | 562/412 |
| 3,235,588 | 2/1966 | Weaver | 260/525 |
| 3,665,030 | 5/1972 | de Radzitzky d'Ostrowick | 260/488 |
| 3,816,523 | 6/1974 | Sidi | 562/414 |
| 4,007,228 | 2/1977 | Feld | 260/524 |
| 4,398,037 | 8/1983 | Takeda et al. | 560/77 |
| 4,603,220 | 7/1986 | Feld | 562/416 |

FOREIGN PATENT DOCUMENTS 1005315 9/1965 United Kingdom .

OTHER PUBLICATIONS

Sasson, J. Org. Chem., 51, pp. 2880–2883, (1986).
Chem. Abst., 93:71220c.
Hydrocarbon Processing, p. 134, (11–1977).
Messina, Hydrocarbon Processing, 43(11), pp. 191–192, (1964).
Hydrocarbon Processing, Nov. 1977, p. 134, Snis–Viscosa, "Benzoic Acid".
Hydrocarbon Processing, Nov. 1964, vol. 43, No. 11, pp. 191–192, Snis–Viscosa, "Upgrade Toluene to Benzoic Acid" by G. Messina.

Primary Examiner—Michael L. Shippen
Attorney, Agent, or Firm—Morgan & Finnegan

[57] ABSTRACT

A process for the manufacture of benzoic acid is described. The process is based on the reaction of toluene in a liquid phase oxidation with an oxygen containing gas in the presence of a phase-transfer catalyst (a), a transition metal salt (b) and traces of a polar solvent, such as water, the molar ratio between (a) and (b) being in the range of between 0.25:1 to 1.5:1. The phase-transfer catalyst is selected from quaternary ammonium and phosphonium salts having a total carbon atoms in the range of 17 to 58, the anion bound thereto being selected from $Br^-$, $F^-$, $Cl^-$, $OH^-$, $CH_3COO^-$ or $HSO_4^-$. The benzoic acid produced is characterized by its very high purity and high conversion reaching generally values of above 95%.

14 Claims, No Drawings

PROCESS FOR THE MANUFACTURE OF BENZOIC ACID AND SALTS THEREOF

This is a continuation of co-pending application Ser. No. 07/216,116, filed on July 7, 1988, now abandoned.

The present invention relates to a simple process for the manufacture of benzoic acid and salts thereof. More particularly the invention relates to a simple process for the manufacture of benzoic acid and salts thereof at high conversion and of high purity from toluene.

BACKGROUND OF THE INVENTION

The main procedure for the manufacture of benzoic acid is based on the liquid phase oxidation with air or oxygen of toluene in the presence of metallic catalyst(s). Catalysts which were found suitable for this oxidation are generally selected from salts of metals having variable valency such as chromium, cobalt, manganese, lead, iron, copper, nickel and vanadium. Also various compounds of cerium, selenium silver zinc and uranium were suggested.

In addition to the catalyst(s) sometimes a promoter is utilized generally being a bromine-affording substance such as elemental, or inorganic form. Typical examples of such promoters are sodium bromide, potassium bromide, ammonium bromide, manganese bromide or the like.

The literature is quite abundant with various patents on processes for the manufacture of benzoic acid. According to U.S. Pat. No. 3,816,523, toluene is reacted with an oxygen-containing gas in the liquid phase in the presence of a heavy metal salt(cobalt acetate, cobalt naphthenate, manganese acetate and the like) at a temperature in the range of about 130° to 200° C. and a pressure of about 1.5 to 20 atmospheres. Conversion up to 45% is claimed to be obtained. The benzoic acid is distilled out at a pressure in the range of 50 mm to 760 mm.

According to German Offen. No. 3,128,147, toluenes are oxidized in the presence of a soluble cobalt or manganese salt, acetic acid and sodium bromide under a pressure of 20 atmospheres at a temperature of between 125°-130° C. for 220 minutes.

According to the process used by Snia-Viscosa as described in Hydrocarbon Processing, 43, 11, 191, 1964 and 56, 11, 134, 1977, cobalt acetate dissolved in water is utilized as catalyst in the oxidation of toluene by air. The product contains about 30-35% benzoic acid which is recovered either by stripping, crystallization or by fractional distillation, the unreacted toluene being recycled.

According to a recent U.S. Pat. No. 4,398,037 toluene is oxidized in the presence of cobalt acetate as catalyst and co-presence of a lithium compound. As mentioned therein, the absence of an aliphatic carboxylic acid is required.

In a theoretical review "Liquid-phase oxidation of deactivated methylbenzene by aqueous sodium hypochlorite catalyzed by ruthenium salts under phase transfer catalytic conditions" (Journal of Organic Chemistry, 1986, 51, 2880), there are presented some kinetic studies on the reaction in the presence of tetrabutyl ammonium bromide. Of course, the use of an aqueous solution of sodium hypochlorite as an oxidizing reagent is of little value from an industrial point of view.

In the manufacture of benzoic acid, as in other chemical products, two main factors are generally considered: conversion and yield as well as purity of the resulted product. Thus for example, in case of pure benzoic acid produced from toluene by liquid phase oxidation, conversions in the range of between 30% to 45% are obtained while the unreacted toluene is recycled. The benzoic acid produced contains as main impurities: benzaldehyde, benzyl esters, unreacted toluene, tars and other oxygenated compounds. Various methods for the purification of the benzoic acid are known. Thus according to U.S. Pat. No. 3,235,588, the crude benzoic acid in the molten state, is contacted with water at a temperature in the range of between 95°-117° C. After cooling the purified benzoic acid is separated from the aqueous phase. Obviously, the additional purification steps of the benzoic acid will increase significantly the operational costs.

It is an object of the present invention to provide a simple process for the manufacture of benzoic acid and salts thereof from toluene. It is another object of the present invention to provide a simple process for the manufacture of benzoic acid and salts thereof at high conversion. It is yet another object of the present invention to provide a simple process for the manufacture of benzoic acid and salts thereof of a high purity.

BRIEF DESCRIPTION OF THE INVENTION

The invention relates to a process for the manufacture of benzoic acid and salts thereof of a high purity from toluene by a liquid phase oxidation of toluene using an oxygen-containing gas, being carried out in the presence of a phase-transfer catalyst and traces of a polar solvent able to solubilize the catalyst, the process being characterized in that the oxidation reaction occurs at an oxygen partial pressure below 50 atmospheres, in the presence of a catalytic system comprising:
(a) a quaternary onium salt having the general formula:

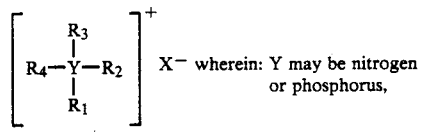

$R_1$ is alkyl and $R_2$, $R_3$ and $R_4$ may be the same, different or interlinked, selected from alkyl, hydroxyalkyl, aryl or aralkyl group having a total number of carbon atoms in the range of between 17 and 58, and $X^-$ is selected from $F^-$, $Cl^-$, $Br^-$, $OH^-$, $CH_3COO^-$ and $HSO_4^-$ provided that when $Br^-$ is absent from the system a bromide or bromine is added, and (b) a transition metal salt, the molar ratio between (a) and (b) being in the range of between 0.25:1 to 1.5:1. The above quaternary onium salts, possessing between 17 and 58 carbon atoms, are characterized by their lipophilicity which enables the extraction of the transition metal salt. The most preferable phase-transfer catalysts are the quaternary onium salts having between 20 and 48 total carbon atoms.

Typical examples of ammonium quaternary bromides and chlorides are: di-n-decyldimethyl ammonium bromide, tri-n-octylmethyl ammonium bromide, tetra-n-hexyl ammonium bromide, tetra-n-octyl ammonium bromide, tri-n-hexyl-2-hydroxyethyl ammonium bromide, phenyl-tri-n-octyl ammonium bromide, tri-n-decyl ammonium bromide, tetra-n-dodecyl ammonium bromide, tetra-n-nonyl ammonium bromide, tetra-n-hexadecyl ammonium bromide, phenyl-tri-n-hexylammonium bromide, benzyl-tri-n-octylammonium bromide, phenyl-tri-n-decyl ammonium chloride, tri-n-dodecyl-2-hydroxyethyl ammonium chloride, n-hexadecylpyridinium bromide, etc. Most of these quaternary ammonium salts are also commercially available at reasonable costs. Among the quaternary phosphonium bromides and chlorides the following can be mentioned: tetra- n-hexylphosphonium bromide, tetra-n-octylphosphonium bromide, phenyl-tri-n-hexylphosphonium chloride, n-hexadecyl-tri-n-butylphosphonium bromide, tetra-n-hexylphosphonium bromide, etc.

It was found that the iodide quaternary onium salts are substantially ineffective as phase-transfer catalyst for the process according to the present invention. It seems that in the presence of the transition metal salt the catalytic activity of the quaternary phosphonium iodide is greatly affected. Example 18 using quaternary phosphonium iodide, under the same conditions as in the present invention, clearly illustrates this matter. This is quite surprising and the inventors are not yet in a position to explain this anomaly.

In the German Patent No. 1,263,003 it is claimed a process for the catalytic oxidation of hydrocarbons at a temperature in the range of 0° to 250° C. using phosphonium quaternary salts. The presence of acetic acid is mentioned to be optionally required in view of the high pressure prevailing in the system. In the example for the oxidation of toluene, the iodide phosphonium salt is utilized in the presence of a large amount of acetic acid (10 times on the amount of toluene) under an oxygen partial pressure of 50 atmospheres. The mechanism involved in this oxidation seems to be based on the activation of the phosphonium catalyst by the high pressure used in this system. It was also found that the corresponding phosphonium bromide salt gave under the conditions of the present invention only poor conversions of about 5 to 10%.

Other phase transfer catalysts which may be used are for example, crown ethers (macrocyclic polyethers) which are described in detail in the "Journal of the American Chemical Society", 89, 7017 (1967).

The transition metal to be used in the catalytic system is selected from manganese, cobalt, molybdenum, chromium, vanadium, tungsten, cerium or mixtures thereof. Most preferred are chromium and cobalt. The amount of transition metal salt can be selected in a very broad molar ratios range such as between 1:1000 to 1:100 (transition metal to the toluene) and preferably between 1:500 to 1:200. The transition metal salt is preferably in the hydrated form containing water of crystallization.

The anion to which the transition metal is bound, is not critical and may be selected from any inorganic or organic moiety provided that the corresponding salt can be solubilized in the reaction system. Particularly preferable are: bromides, acetates, chlorides, sulfates, and the most preferred are the bromides; all of these salts are commercials available in bulk.

The oxidation may be carried out with pure oxygen gas or preferably with a gaseous mixture containing lower concentrations of oxygen such as, for example, air.

The phase-transfer catalyst has a very important role in the process according to the present invention. It has the role to form an organic soluble adduct with a catalytic activity which does promote the oxidation reaction. As known, a phase-transfer catalyst is defined as a substance which promotes reaction by transferring substance from one phase to another phase where it undergoes the desired reaction. According to the present invention it was found that the transition metal salt is solubilized in the organic phase in the form of an onium adduct. In this manner, it catalyses the oxidation reaction.

The quaternary onium salt may be added such as, or prepared in-situ, for example, in case of ammonium salt by including in the reaction system a tertiary amine and an alkylating agent.

In order to initiate the reaction, the process according to the present invention does involve the addition of traces of a polar solvent such as minor amounts of water preferably in the form of water of crystallization present with the metal salt. The amount of polar solvent should be sufficient to dissolve the metal salt as a saturated solution under the reaction conditions. It has been found that an increase in the amount of water in the system, beyond the saturation, decreases the reaction rate and generally should be avoided.

The process according to the present invention is characterized by its very high conversion generally of above 95% and even above 99%. It was also found that the benzoic acid produced is substantially pure containing only minor amounts of by-products usually encountered in the prior art methods. In this manner, additional purification steps will be significantly reduced for certain applications.

The invention is particularly useful for the oxidation of toluene into benzoic acid. However, one may conceive to start with oxidation products of toluene such as benzyl alcohol and aldehyde-substituted aromatic compounds such as benzaldehyde or any mixture thereof, which can be obviously also oxidized according to the present process.

It was surprisingly found that the conversion of the toluene into benzoic acid, is correlated to the molar ratio between the phase-transfer catalyst (a) and the transition metal salt (b). It was found, that conversion of above 60% are obtained when said ratio is about 0.35, reaching above 90% when said ratio (a):(b) is about 0.8. Above this ratio, there is a sudden decrease in the conversion rate which can reach even a value close to zero when the above ratio is about 2:1. The molar ratio of (a):(b) to be used in the process according to the present invention is in the range of between 0.25 : 1 to 1.5:1 and preferably 0.4:1 to 1.15:1.

The use of bromide ion as a promoter in the liquid phase oxidation of toluene leads to corrosion of the apparatus and will impose corrosion-resistant equipment. According to the present invention, in which the bromide ion is, or becomes bound to a quaternary onium moiety, this problem is substantially alleviated in view of the absence of an aqueous phase.

The oxidation reaction according to the present invention is carried out either batchwise or continuously at an elevated temperature in the range of 100° to 200° C. and preferably in the range of 120° to 170° C. Also, elevated pressure will be required e.g. in the range of 1 to 100 atmospheres (air) and preferably 10 to 50 atmospheres corresponding to an oxygen partial pressure in the range of 2 to 10 atmospheres. However, the oxygen partial pressure should not exceed 50 atmospheres.

The entire process is very simple to be carried out and requires standard equipment as used for these types of products. The reactor consists of an autoclave provided with a stirrer and condenser. The autoclave has a jacket through which heated oil or cooled water are circulated the temperatures being controlled by a thermostat. The gaseous reactants are introduced through a sparger and the out-gases through a needle valve and flow meter. Samples can be drawn through a sampling valve. The reactants: toluene, transition metal salt and phase-transfer catalyst, are conveyed into the vessel followed by the introduction of air. The vessel is heated to about 130° C., whereby an increase of the pressure to about 15 atmospheres can be noticed. Upon the beginning of the reaction, the temperature increases to about 160° C. The evolving vapors containing toluene and water, are condensed, the toluene being recycled while the water is removed from the reaction system. After 2-3 hours, under continuous flow of air, the temperature drops by itself which indicates the end of the reaction. The further handling of the reaction products may be carried out in two different ways:

According to one embodiment the reaction product is distilled under vacuum. The residual distillate does contain the catalyst and could be recycled to a further cycle of toluene oxidation. In this manner, the catalyst can be used a number of times, that is, one can for instance recover it together with the oxidation product, separate out from the reactor, and utilize it again in the oxidation process.

According to another embodiment, an aqueous alkaline solution (15-30% by weight) is added to the cooled reaction product. Preferred alkaline compounds are sodium hydroxide, potassium hydroxide and ammonium hydroxide. The slurry is filtered and the separated solid comprising the catalyst is removed. The filtrate obtained is treated with a concentrated solution of an acid, preferably a mineral acid, whereby precipitated benzoic acid is separated. This second alternative will produce a benzoic acid of a very high purity, even of above 99.8%. A person skilled in the art will select the proper mode of benzoic acid separation and catalyst recovery according to the specific requirements and availabilities at site.

The entire process can be carried out in a continuous manner which has clear advantages from an industrial point of view.

While the invention will now be described in connection with certain preferred embodiments in the following Examples it will be understood that it is not intended to limit the invention to these particular embodiments. On the contrary it is intended to cover all alternatives, modifications and equivalents as may be included within the scope of the invention as defined by the appended claims. Thus, the following Examples which include preferred embodiments will serve to illustrate the practice of this invention, it being understood that the particulars described are by way of example only and for purpose of illustrative discussion of preferred embodiments of the present invention.

In the Examples the concentrations and figures given are by weight unless otherwise stated.

Examples 17 and 18 do not illustrate the invention and are presented only for comparison purposes, to show the extent of conversion when phase-transfer catalysts not included in the claims of the present invention are used.

EXAMPLE 1

Preparation of benzoic acid

The equipment consisted of an autoclave (1 liter) equipped with a jacket and oil circulating thermostat, magnetic drived stirrer, water cooled condenser and liquid separator, sparger for introducing gaseous reactants, outlet for gas with needle valve and flow meter and sampling valve.

The following reagents were introduced into the autoclave 207 g toluene (2.25 mole), 1.07 gr cobalt chloride hexahydrate (4.5 m mole), 2.7 g didecyldimethyl ammonium bromide (50% w/w in toluene—3.35 moles—). The system was charged with air (12 atm.) and warmed to 135° C., the pressure increased due to heating to 15 Atm. Air was allowed to skip from the system at a rate of 2 l/min (STP). As the reaction started the temperature increased to 160° C. After 3 hours with continuous flow of air the temperature dropped to 135° by itself. After cooling, 450 ml of 20% aqueous NaOH were added to the mixture and the slurry was filtered to remove the solid precipitate of the catalyst. The solution was acidified with HCl (32%) to a pH of 3.4 and the precipitated benzoic acid was dried in vacuum to yield 252 g (92% yield) of 99.5% pure benzoic acid. Gas chromatography (on methyl-silicon in a capillary of 50 m) showed the absence of benzyl benzoate, benzaldehyde and benzyl alcohol.

EXAMPLE 2

Preparation of benzoic acid

The experiment as in Example 1 was repeated using the same equipment, amounts of reagents and procedure concerning the toluene oxidation. In this case the separation of the reaction products was carried out as follows:

The reaction mixture was distilled under vacuum (20 mm Hg) to yield 273 g (99% yield) of benzoic acid. The melting point of the product was 122° C. Analysis of the product as determined by gas chromatogaphy (on methylsilicon in a capillary of 50 m) showed that it consisted of 99.6% pure benzoic acid which was free of benzyl benzoate, benzaldehyde and benzyl alcohol.

Using this alternative the remaining of the distillation containing the catalyst could be directly recycled to another cycle.

EXAMPLE 3

Preparation of sodium benzoate

In the same equipment as in Example 1, the following reagents were introduced: 184 g of toluene, 0.95 g of cobalt chloride hydrate and 1.14 g of didecyldimethyl ammonium bromide. The mixture was heated to about 100° C. under a pressure of 15 atmospheres air. The reaction was continued for about two hours the temperature increasing to about 160° C. After cooling to about 80° C., the benzoic acid produced was neutralized with a stoichiometrically amount of a solution of sodium hydroxide (15% by wt.).

After separating the catalyst adduct precipitate, the filtrate was treated with benzoic acid adjusting the pH to about 6.5. An amount of 259 g of sodium benzoate, corresponding to a yield of 90%, was recovered. The purity of the product, as determined by gas chromatography (the same adsorbent as in Example 1) was 99.8%.

EXAMPLE 4

Preparation of benzoic acid

In the same equipment as in Example 1, the following reagents were introduced:

207 g of toluene (2.25 moles); 1.6 g of cobalt chloride hexahydrate (6.7 mmoles) and 2.2 g of tetrahexyl ammonium bromide (5 mmoles). The mixture was heated to about 140° C. under a pressure of 15 atmospheres air. The reaction was continued for about 5 hours, the temperature increasing to about 155° C.

After cooling the reaction mixture was analyzed and found to consist of 85% moles of benzoic acid, 2% moles of benzaldehyde, 1% mole of benzyl alcohol and 12% of unreacted toluene.

EXAMPLE 5

The experiment as in Example 1 was repeated but the phase transfer catalyst consisted of 2.7 g of tetraoctyl ammonium bromide (instead of 2.7 g of didecyldimethyl ammonium bromide).

After 5 hours the reaction mixture was analyzed and was found to consist of: 93% moles of benzoic acid, 2% moles of benzaldehyde, 1.2% moles benzyl alcohol and 3.8% moles of unreacted toluene.

EXAMPLE 6

In the same apparatus as in Example 1, the following reagents were introduced:

207 g of toluene (2.25 moles); 2.0 g of didecyldimethyl ammonium bromide, and 1.7 g of cobalt acetate tetrahydrate. The mixture was charged with air (12 atmospheres) and heated to 140° C. for about 4 hours. The final temperature increased up to 168° C.

After cooling the reaction mixture was analyzed and found to contain 99.5% benzoic acid.

EXAMPLE 7

The experiment as in Example 1, was repeated using the following reagents:

207 g of toluene., 9 g of didecyldimethyl ammonium bromide, and 5.6 g of chromium chloride hexahydrate. The reaction was carried out under a pressure of 10 atmospheres air, the temperature being about 120° C. The reaction was continued for about 8 hours under these conditions.

After cooling, the reaction mixture was analyzed and found to contain 89% benzoic acid, 10% benzaldehyde and 1% benzyl alcohol.

EXAMPLE 8

The experiment as in Example 1 was repeated using the following reagents:

207 g of toluene; 5.6 g of chromium chloride hexahydrate and 9 g of didecyl ammonium bromide.

The reaction mixture was agitated for about 5 hours at 150° C. (under 15 atmospheres air, air being allowed to skip at a rate of 2.0 l/min (STP).

After cooling the mixture was analyzed and found to contain 80% benzoic acid, 14% benzaldehyde, 4% benzyl benzoate, and 2% benzyl alcohol (mole percentages).

EXAMPLE 9

In this experiment, the use of a phase-transfer catalyst prepared in-situ is illustrated.

In the same reactor as in Example 1, containing 10 g of toluene, the following reagents were dissolved: 0.82 g of n-hexyl bromide and 1.38 g of tri- (n-hexyl) amine. The reaction mixture was heated for about 4 hours at 120° C. To the mixture, there were added 197 g of toluene and 1.6 g of cobalt chloride hexahydrate. The mixture was charged with air (15 atmospheres) air being allowed to skip at a rate of 2.0 l/min (STP); the heating was continued for about 9 hours at 140° C. After cooling, the product was analyzed and found to contain 98% benzoic acid and 2% benzaldehyde (mole percentages).

EXAMPLE 10

The experiment as in Example 1 was repeated using the following reagents:

207 g of toluene; 1.7 g of cobalt chloride hexahydrate (6.7 mmole) and 2.25 g of tetrahexyl phosphonium bromide.

The reaction mixture was agitated for about 6 hours at 160° C. (under 17 atmospheres air), air being allowed to skip at a rate of 2.5 l/min (STP).

After cooling the product (208 g) was analyzed and found to consist of 99.8% benzoic acid.

EXAMPLE 11

The experiment as in Example 1 was repeated using the following reagents:

414 g of toluene (4.5 moles), 4 g of cobalt chloride hexahydrate (16.8 mmoles) and 9.5 g tetra-n-dodecylammonium bromide. The reaction mixture was heated for about 7 hours at 165° C. The mixture was charged with air (18 atmospheres) air being allowed to skip at a rate of 2.7 l/min (STP).

After cooling the reaction mixture obtained was conveyed to a distillation unit. The distillation was carried out under vacuum (20 mm Hg) obtaining 451 g of pure benzoic acid at a yield of 92.4%. The residue containing the catalyst was reused in another cycle of toluene oxidation.

EXAMPLE 12

The experiment as in Example 1 was repeated using the following reagents:

207 g toluene (2.25 moles), 2,2 g of cobalt bromide hexahydrate (6.7 mmoles) and 2.23 g of tetra-n-hexylammonium hydrogen sulfate. The reaction mixture was heated for about 5 hours at 160° C. under a pressure of 20 atmospheres air with a constant flow of 3 l/min (STP).

After cooling the reaction mixture was distilled under vacuum to yield 252 g of benzoic acid (yield 91.8%) with a purity of 99%.

EXAMPLE 13

The experiment as in Example 1 was repeated using the following reagents:

207 g toluene (2.25 moles), 2,2 g of cobalt bromide hexahydrate (6.7 mmoles) and 2.38 g of tetra-n-hexylammonium benzoate (5 mmole). The reaction mixture was heated for about 6 hours at 160° C. under a pressure of 20 atmospheres air with a constant flow of 3 l/min (STP).

After cooling the reaction mixture was distilled under vacuum to yield 250 g of benzoic acid (yield 91%) with a purity of 99.1%.

EXAMPLE 14

The experiment as in Example 12 was repeated, using the same amount of toluene the other reagents being:
- 1.6 g of cobalt chloride hexahydrate (6.7 mmoles), and
- 2.4 g of tri-n-octyl-2-hydroxyethylammonium bromide (5 mmoles).

The reaction mixture was mixed in the autoclave at 160° C. for about 7 hours under a pressure of 18 atmospheres (air) with a constant flow of 2.1 l/min.

After cooling, the mixture was distilled under vacuum to yield 240 g of pure benzoic acid (99.8%) the yield being 87.4%.

EXAMPLE 15

The experiment as in Example 14 was repeated using the same amounts of toluene and cobalt chloride hexahydrate, but the phase transfer catalyst used was 2.63 g of benzyl tri-n-octylammonium bromide (5 mmoles).

The reaction mixture was mixed in the autoclave at 160° C. for about 7 hours under a pressure of 18 atmospheres (air) with a constant flow of 2.3 l/min.

After cooling, the mixture was distilled under vacuum to yield 243 g of pure benzoic acid (99.8%) the yield being 88.5%.

EXAMPLE 16

The experiment as in Example 12 was repeated using the same amounts of toluene and cobalt chloride hexahydrate but the phase transfer catalyst used was 1.99 g of tetra-n-hexylphosphonium chloride.

The reaction mixture was mixed in the autoclave at 165° C. for about 6 hours under a pressure of 15 atmospheres (air) with a constant flow of 2.4 l/min.

After cooling, the mixture was distilled under vacuum to yield 245 g of pure benzoic acid (99.8%) the yield being 89.2%.

EXAMPLE 17

A comparative experiment was carried out using a phase-transfer catalyst possessing 16 carbon atoms, i.e. outside the present invention. The reaction was carried in the same equipment as in the previous Examples using the following reagents:

207 g of toluene (2.25 moles), 1.6 g cobalt chloride hexahydrate (6.7 mmole) and 1.6 g tetrabutyl ammonium bromide (5 mmole).

The reaction was conducted at 140° C., at 15 atmospheres for about 5 hours Air was allowed to skip from the system at a rate of 2.0 l/min (STP).

After cooling the product was analyzed and found to contain only less than 5% benzoic acid together with about 95% of unreacted toluene.

Although the molar ratio between the phase-transfer catalyst and metal salt was adequately selected, the very low conversion is explained by the fact that the phase-transfer catalyst did not extract the metal salt into the organic phase since this catalyst does not possess sufficient lipophicity.

EXAMPLE 18 (comparative example)

The experiment as in Example 1 was repeated using the following reagents:
- 207 g toluene (2.25 moles),
- 1.6 g of cobalt chloride hexahydrate (6.7 mmoles), and
- 2.45 g of tetra-n-hexylphosphonium iodide (5 mmoles).

The above reagents were mixed in the autoclave at 160° C. for about 6 hours under a pressure of 20 atmospheres (air) with a constant flow of 3 l/min.

After cooling, the mixture was analyzed and found to contain only less than 10% benzoic acid (% moles).

We claim:

1. A process for the manufacture of benzoic acid and salts thereof of a high purity from toluene by a liquid phase oxidation of toluene using an oxygen-containing gas, being carried out in the presence of a phase transfer catalyst selected from the group consisting of a quaternary onium salt and a crown ether, and traces of a polar solvent able to solubilize the catalyst, the polar solvent being water, the process being characterized in that the oxidation reaction occurs at an oxygen partial pressure below 50 atmospheres in the presence of a catalytic system comprising:

(a) a quaternary onium salt having the general formula:

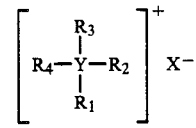

wherein: $R_1$ is alkyl and $R_2$, $R_3$ and $R_4$ may be the same or different, selected from an alkyl, a hydroxyalkyl, an aryl or an aralkyl group, $R_1$, $R_2$, $R_3$ and $R_4$ having a total number of carbon atoms from 17 to 58, Y is selected from nitrogen or phosphorus, and X is selected from $F^-$, $C^-$, $Br^-$, $OH^-$, $CH_3$, $COO^-$ and $HsO^-_4$ provided that when $Br^-$ is absent from the system a bromide or bromine is added;

(b) a transition metal salt, the molar ratio between (a) and (b) being from 0.25:1 to 1.5:1.

2. A process according to claim 1, wherein said quaternary onium salt has a total number of carbon atoms from 20 to 48.

3. A process according to claim 1 wherein said quaternary ammonium salt is formed in-situ.

4. A process according to claim 1, wherein the transition metal is selected from the groups 4 to 6 of the periodic Table.

5. A process according to claim 1, wherein said transition metal is selected from the group consisting of manganese, cobalt, molybdenum, chromium, vanadium, tungsten, cerium or mixtures thereof.

6. A process according to claim 1, wherein the anion bound to said transition metal is selected from chloride, bromide, acetate and sulfate or mixtures thereof.

7. A process according to claim 5, wherein said transition metal salt is hydrated cobalt chloride.

8. A process according to claim 1, wherein the molar ratio between the phase-transfer catalyst and transition metal salt is from 0.4:1 to 1.15:1.

9. A process according to claim 1, carried out at a temperature from 120° C. to 170° C.

10. A process according to claim 1, carried out at an oxygen partial pressure from 2 atmospheres to 10 atmospheres.

11. A process according to claim 1, further including the step of treating the reaction product with a solution of metal alkali hydroxide producing a slurry containing the benzoic salt, from which the precipitate containing the catalyst is separated.

12. A process according to claim 11, wherein the metal alkali hydroxide is selected from sodium, potassium, and ammonium hydroxide or mixtures thereof.

13. A process according to claim 1, further including the step of distilling out the benzoic acid product from the reaction mixture and recycling the catalyst to the process.

14. A process according to claim 11, wherein the product obtained is sodium benzoate.

* * * * *

UNITED STATES PATENT AND TRADEMARK OFFICE
CERTIFICATE OF CORRECTION

PATENT NO. : 4,965,406

DATED : October 23, 1990

INVENTOR(S) : Dakka Jihad; Zoran Amikam; Yoel Sasson

It is certified that error appears in the above-identified patent and that said Letters Patent is hereby corrected as shown below:

In the Claims:

Claim 1, Column 10, line 23, "C" should read --Cl--; and

Column 10, line 25, "HsO" should read --HSO--.

Signed and Sealed this

Seventh Day of July, 1992

Attest:

DOUGLAS B. COMER

Attesting Officer

Acting Commissioner of Patents and Trademarks